US012662507B2

(12) United States Patent
Kohgo

(10) Patent No.: US 12,662,507 B2
(45) Date of Patent: Jun. 23, 2026

(54) CYTOSINE-TYPE BRIDGED NUCLEOSIDE AMIDITE CRYSTALS AND METHOD FOR PRODUCING SAME

(71) Applicant: Yamasa Corporation, Choshi (JP)

(72) Inventor: Satoru Kohgo, Chiba (JP)

(73) Assignee: YAMASA CORPORATION, Choshi (JP)

( * ) Notice: Subject to any disclaimer, the term of this patent is extended or adjusted under 35 U.S.C. 154(b) by 461 days.

(21) Appl. No.: 18/265,880

(22) PCT Filed: Dec. 10, 2021

(86) PCT No.: PCT/JP2021/045679
§ 371 (c)(1),
(2) Date: Jun. 7, 2023

(87) PCT Pub. No.: WO2022/124410
PCT Pub. Date: Jun. 16, 2022

(65) Prior Publication Data
US 2024/0083935 A1      Mar. 14, 2024

(30) Foreign Application Priority Data

Dec. 11, 2020    (JP) ................................. 2020-205688

(51) Int. Cl.
*C07H 19/067*          (2006.01)
(52) U.S. Cl.
CPC ........ *C07H 19/067* (2013.01); *C07B 2200/13* (2013.01)
(58) Field of Classification Search
USPC ...................................................... 536/26.8
See application file for complete search history.

(56) References Cited

U.S. PATENT DOCUMENTS 6,268,490 B1      7/2001  Imanishi et al.
2022/0011301 A1    1/2022  Bergmann et al.

FOREIGN PATENT DOCUMENTS

| EP | 1409497 | B1 | 1/2005 | | |
| EP | 1015469 | B1 | 4/2005 | | |
| JP | 10-304889 | A | 11/1998 | | |
| JP | 2002-521310 | A | 7/2002 | | |
| JP | 2004-536125 | A | 12/2004 | | |
| WO | WO-2019224172 | A1 * | 11/2019 | ............. | C07H 19/16 |
| WO | 2020/099533 | A1 | 5/2020 | | |

OTHER PUBLICATIONS

Horiba et al., The Journal Of Organic Chemistry, Nov. 2016, vol. 81(22), pp. 11000-11008. (Year: 2016).*

International Preliminary Report on Patentability issued Jun. 13, 2023 in corresponding PCT application No. PCT/JP2021/045679.
Horiba et al., Synthesis of scpBNA-mC, -A, and -G Monomers and Evaluation of the Binding Affinities of scpBNA-Modified Oligonucleotides toward Complementary ssRNA and ssDNA. J Org Chem. Nov. 18, 2016;81(22):11000-11008.
Koshkin et al., LNA (Locked Nucleic Acids): Synthesis of the adenine, cytosine, guanine, 5-methylcytosine, thymine and uracil bicyclonucleoside monomers, oligomerisation, and unprecedented nucleic acid recognition. Tetrahedron. Apr. 2, 1998;54(14):3607-3630.
Maruzen Inc., Experimental Chemistry (continued) 2 Separation and purification. pp. 159-178, 186-187, Jan. 25, 1967.
Nielsen et al., Alpha-LNA (locked nucleic acid with alpha-D-configuration): synthesis and selective parallel recognition of RNA. Chemistry. Feb. 2, 2002;8(3):712-22.
Riml et al., Synthesis of 5-Hydroxymethylcytidine- and 5-Hydroxymethyl-uridine-Modified RNA. Synthesis (Stuttg). Apr. 2016;48(8):1108-1116.
Sorensen et al., alpha-L-ribo-configured locked nucleic acid (alpha-L-LNA): synthesis and properties. J Am Chem Soc. Mar. 13, 2002;124(10):2164-76.
Takeshita et al., Synthesis of Deoxypseudouridine 5'-Triphosphate Bearing the Photoremovable Protecting Group at the N1 Position Capable of Enzymatic Incorporation to DNA. J Org Chem. Feb. 21, 2020;85(4):1861-1870.
Umemoto et al., Direct and practical synthesis of 2'-O,4'-C-aminomethylene-bridged nucleic acid purine derivatives by transglycosylation. Tetrahedron. Mar. 2, 2017;73(9):1211-1218.
International Search Report and Written Opinion mailed Jan. 18, 2022 in corresponding PCT application No. PCT/JP2021/045679.
European communication dated Nov. 5, 2024 in corresponding European patent application No. 21903506.0.
Threlfall, "Analysis of Organic Polymorphs—A Review," Analyst. vol. 120, pp. 2435-2460, Oct. 1995.

* cited by examiner

*Primary Examiner* — Traviss C Mcintosh, III
(74) *Attorney, Agent, or Firm* — Nields, Lemack & Frame, LLC

(57)          ABSTRACT

A cytosine-type bridged nucleoside amidite crystal represented by the following structural formula:

[Chem 1]

in which $R^1$ and $R^2$ each represents a substituent, and $R^3$ represents a protecting group.

4 Claims, 6 Drawing Sheets

[Fig. 1]
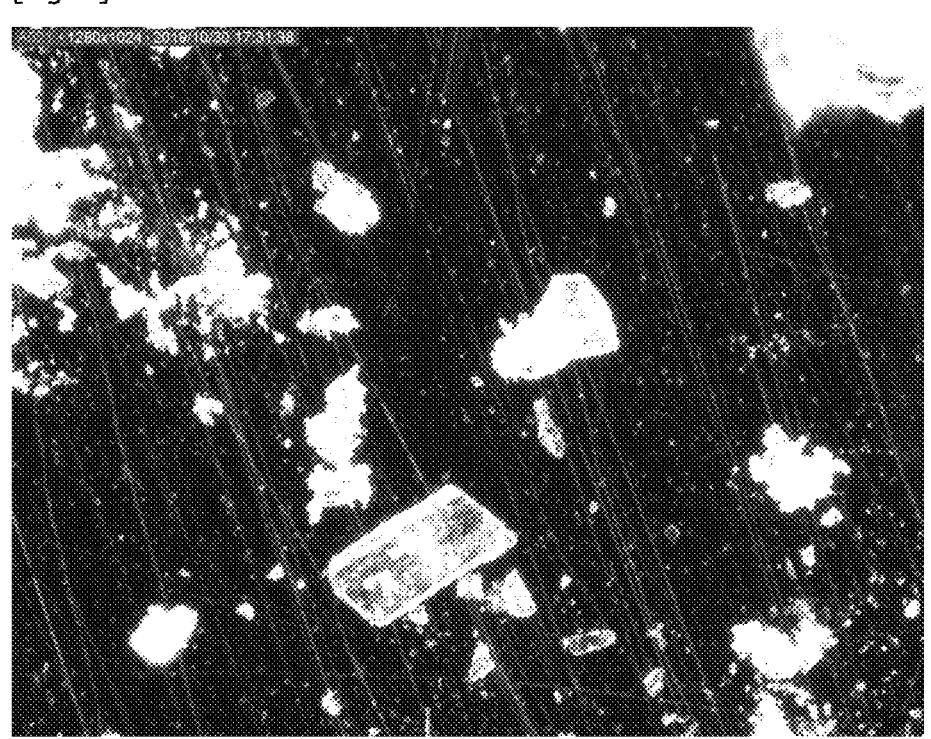

[Fig. 2]
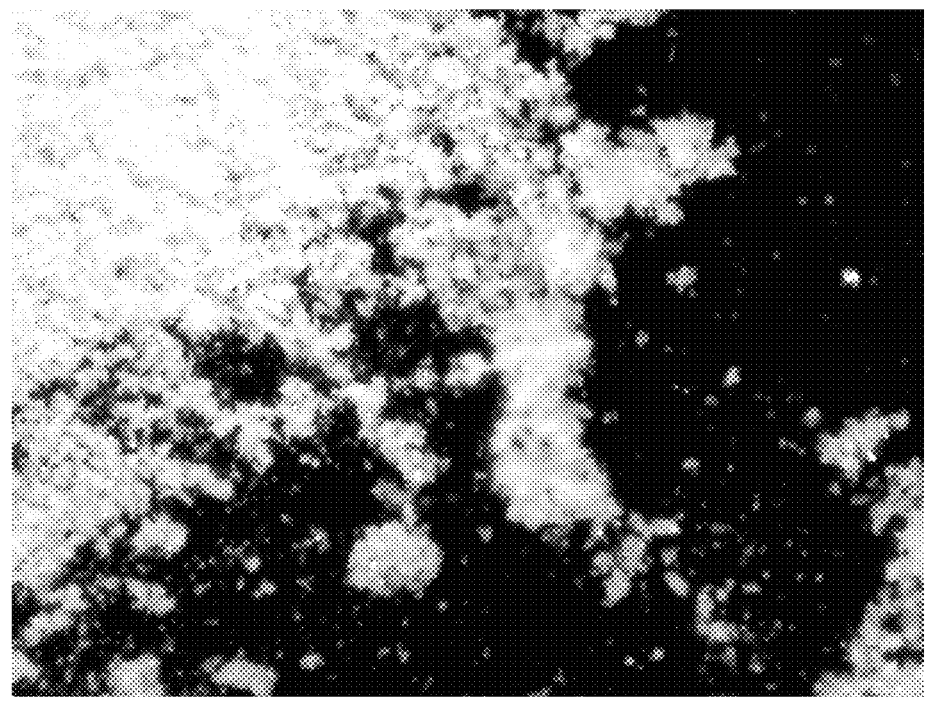
[Fig. 3]
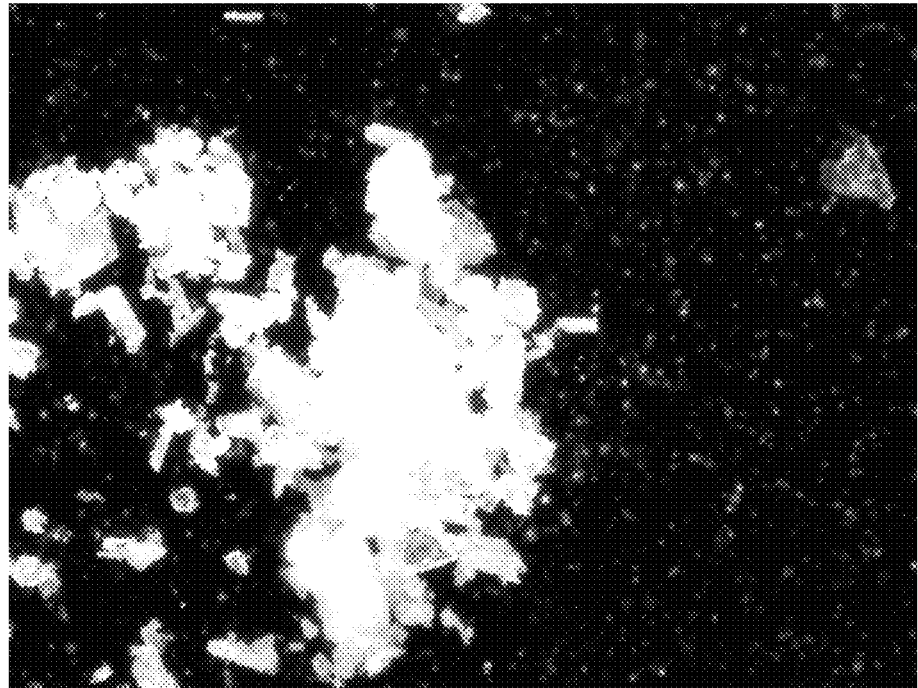

[Fig. 4]
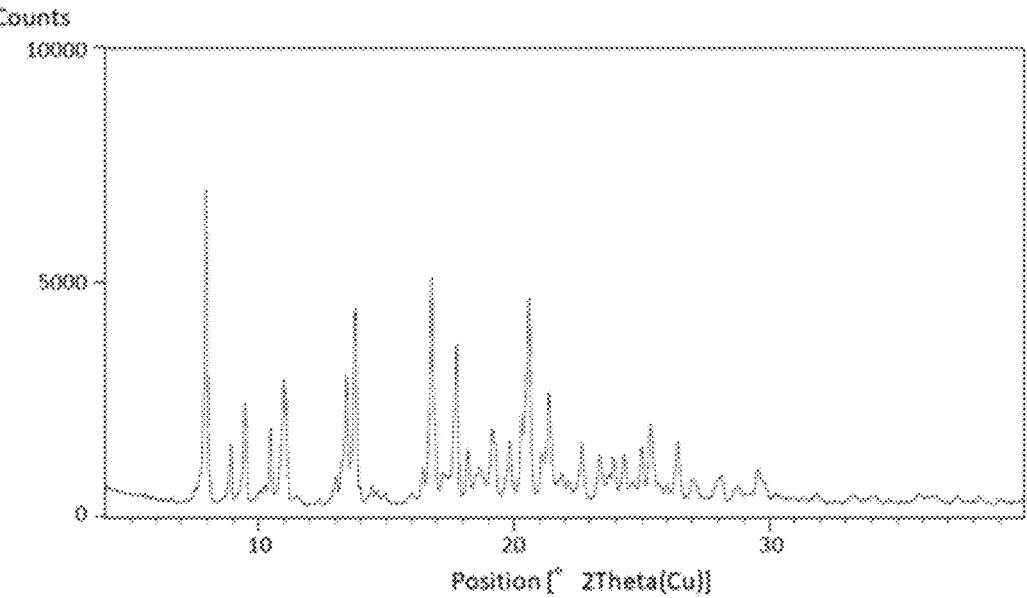
[Fig. 5]
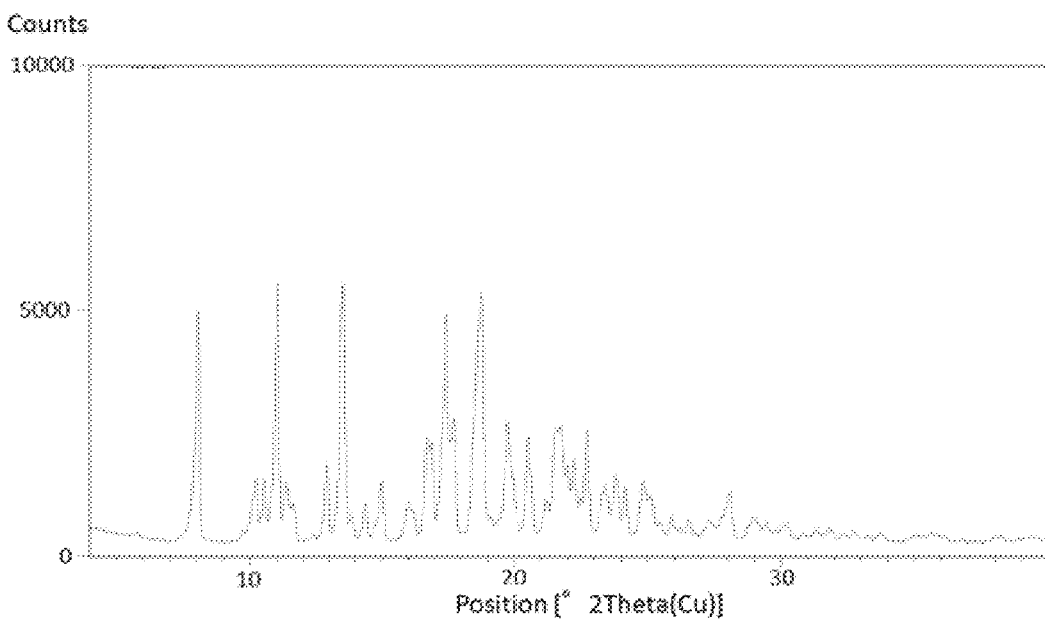

[Fig. 6]
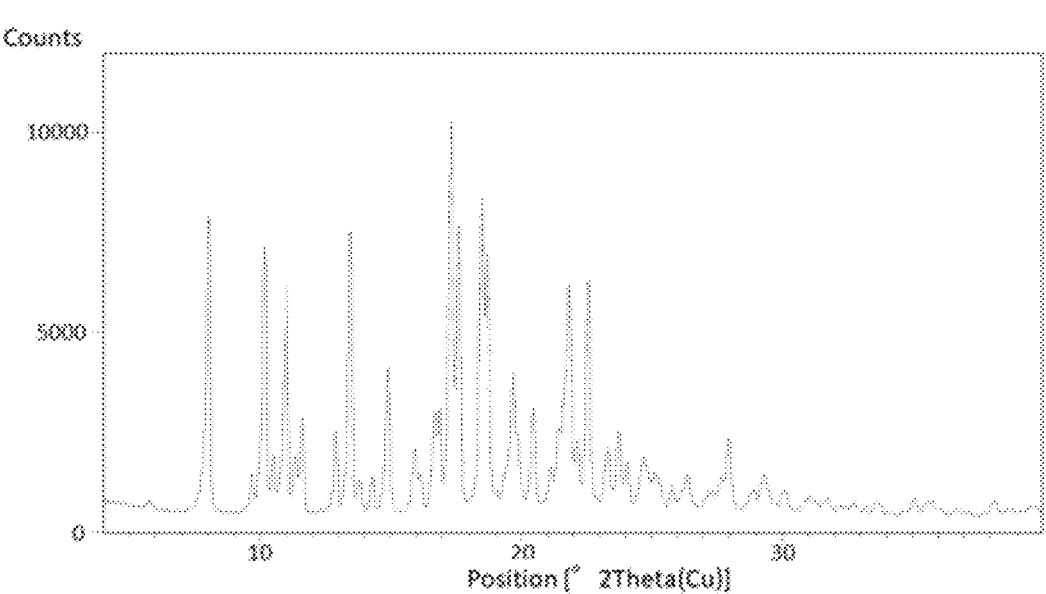
[Fig. 7]
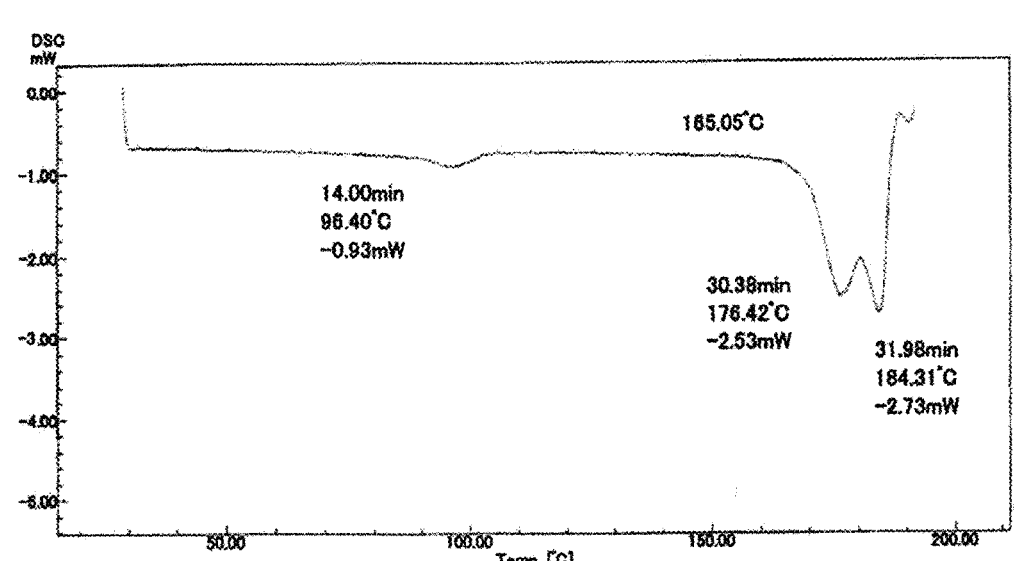

[Fig. 8]

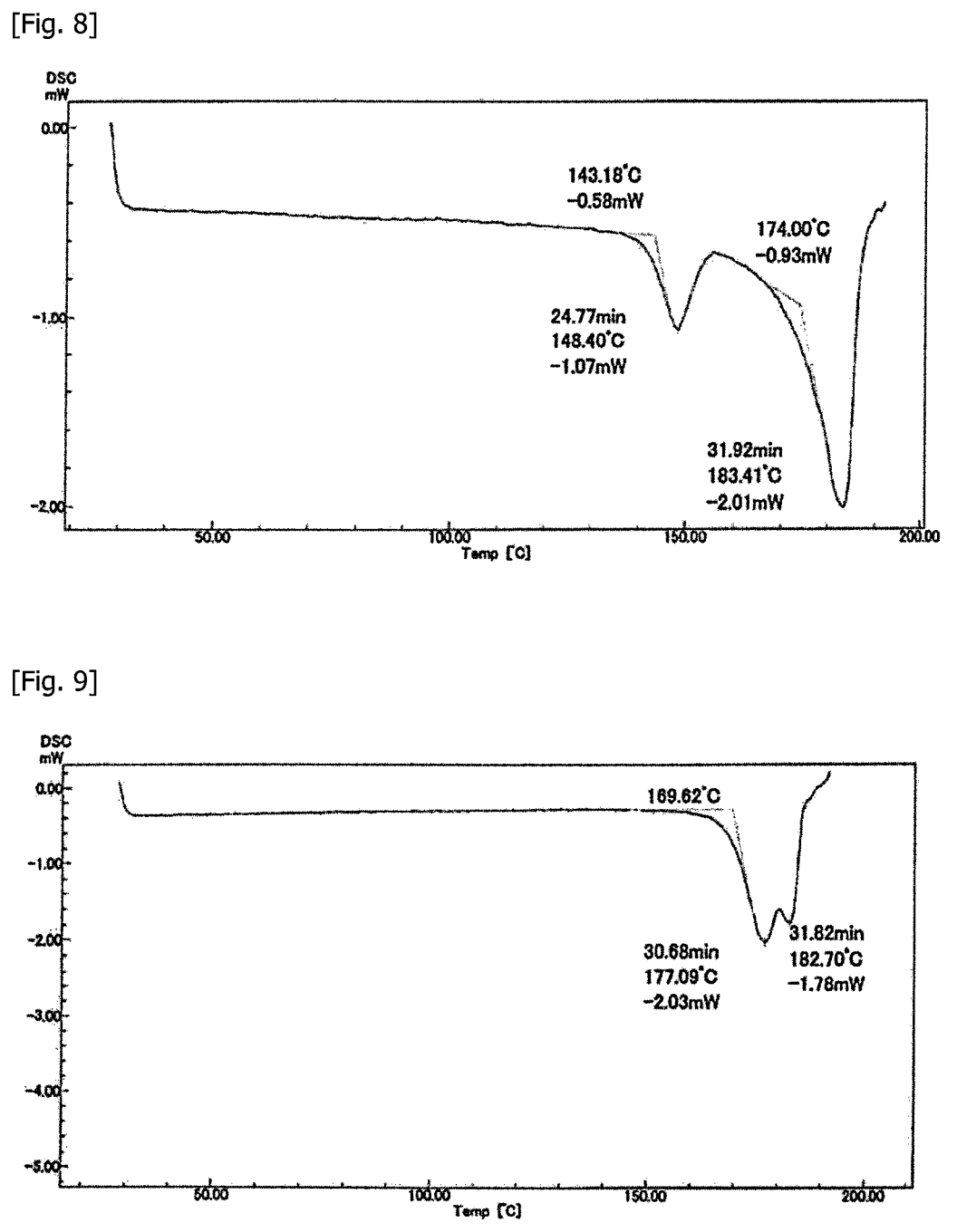

DSC
mW 0.00

143.18°C
−0.58mW 174.00°C
−0.93mW 24.77min
148.40°C
−1.07mW

−1.00

31.92min
183.41°C
−2.01mW

−2.00

50.00          100.00          150.00          200.00

Temp [C]

[Fig. 9]

DSC
mW 0.00

169.62°C

−1.00

−2.00

30.68min
177.09°C
−2.03mW 31.82min
182.70°C
−1.78mW

−3.00

−4.00

−5.00

50.00          100.00          150.00          200.00

Temp [C]

[Fig. 10]
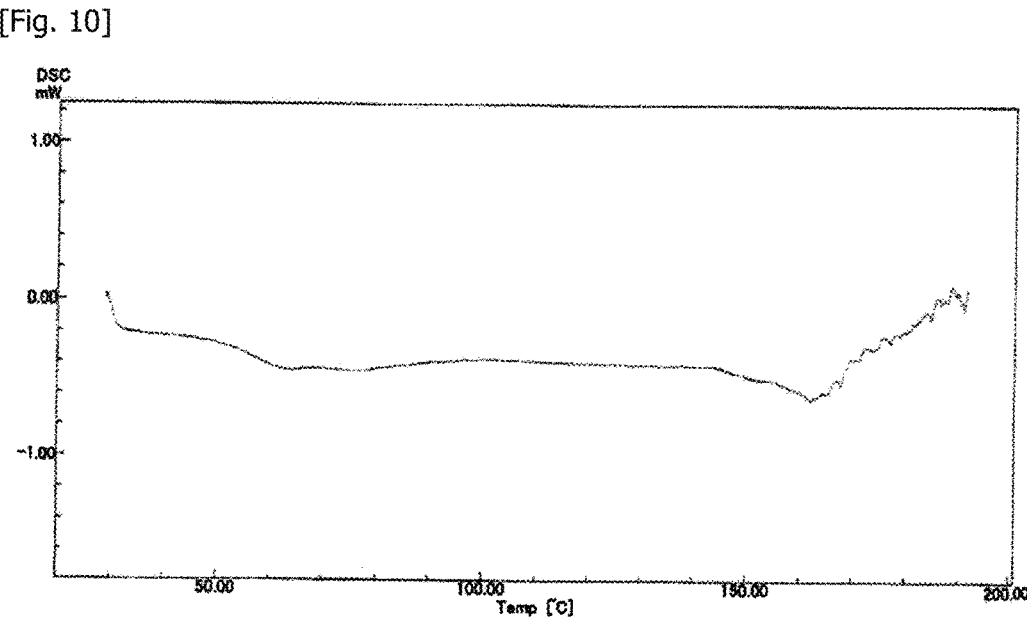
[Fig. 11]
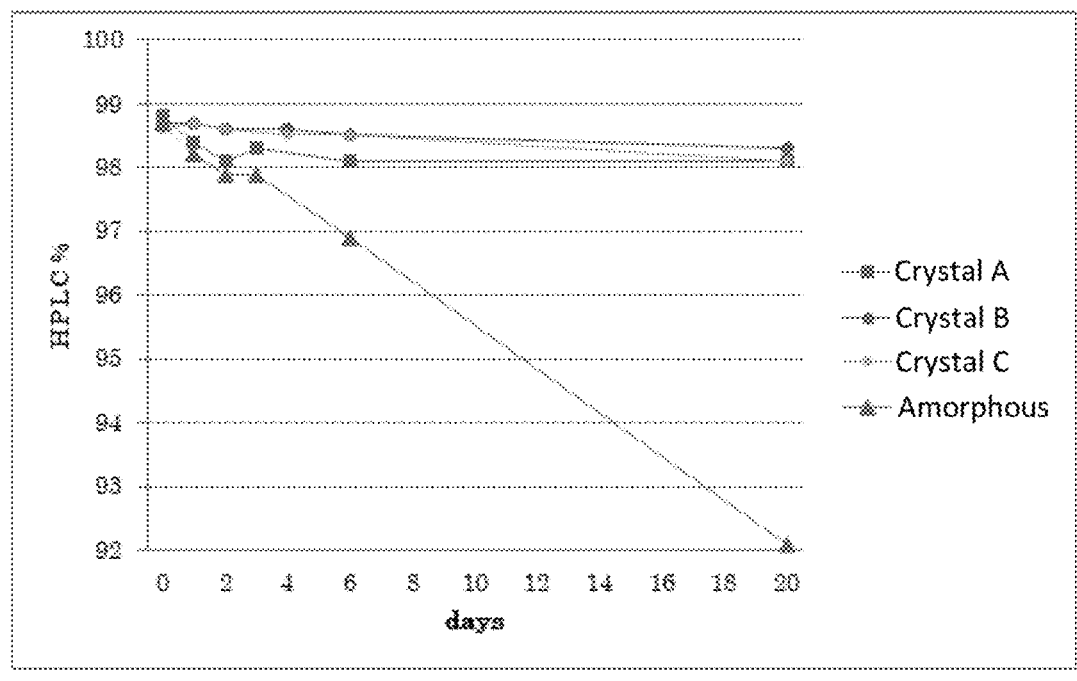

1

CYTOSINE-TYPE BRIDGED NUCLEOSIDE AMIDITE CRYSTALS AND METHOD FOR PRODUCING SAME

TECHNICAL FIELD

The present invention relates to a cytosine-type bridged nucleoside amidite crystals and a method for producing the same.

BACKGROUND ART

There are methods for treating diseases with nucleic acid drugs, including antisense, anti-gene, aptamer, and siRNA methods.

In general, a furanose ring of a nucleoside sugar moiety presents a distorted conformation called an N-type or S-type, rather than a planar structure, and is biased to a particular conformation by substituents on the ring. For example, in the case of a ribonucleoside having a hydroxyl group at the position 2', the N-type conformation is dominant.

Imanishi et al. succeeded in forcibly fixing the conformation of the nucleoside to the N-type by bridging the position 4' and a hydroxyl group at the position 2' of the nucleoside sugar moiety. As a result, it was revealed that LNA (Locked Nucleic Acid) containing the bridged nucleoside formed extremely stable double stranded chains with nucleic acids having complementary sequences (see Patent Literature 1).

The above properties and the like have led to increased expectations for LNA as a material for nucleic acid medicines in recent years.

Synthesis of LNA generally employs a solid-phase synthesis method using an amidite form of a bridged nucleoside, which is called a phosphoramidite method (see Non-Patent Literature 1). In this method, the LNA is synthesized by repeating the cycle of detritylation, then amidite coupling reaction, then cap reaction, and then oxidation (or phosphorothioate) reaction until it reaches a target chain length. That is, the amidite form of the bridged nucleoside is industrially useful because it is used as a starting material for LNA synthesis.

The amidite forms of the bridged nucleosides are distributed in a foamy amorphous form and the like (see Non-Patent Literatures 2, 3, and 4). On the other hand, there is no report that the amidite form of the bridged nucleoside is crystallized.

CITATION LIST

Patent Literature

[PTL 1]
Japanese Patent Application Publication No. H10-304889 A

Non-Patent Literature

[Non-PTL 1]
T. Uemoto, et al, "Direct and practical synthesis of 2'-O,4'-C-aminomethylene-bridged nucleic acid purine derivatives by transglycosylation", Tetrahedron, 2017, vol. 73, p. 1211-1218
[Non-PTL 2]
L. Takeshita, et al., "Synthesis of Deoxypseudouridine 5'-Triphosphate Bearing the Photoremovable Protecting Group at the N1 Position Capable of Enzymatic Incorporation to DNA", J. Org. Chem., 2020, vol.85, p. 1861-1870
[Non-PTL 3]
M. Horiba, et al., "Synthesis of scpBNA-$^mC$, -A, and -G Monomers and Evaluation of the Binding Affinities of scpBNA-Modified Oligonucleotides toward Complementary ssRNA and ssRNA", J. Org. Chem., 2016, vol. 81, p. 11000-11008
[Non-PTL 4]
C. Riml, et al., "Synthesis of 5-Hydroxymethylcytidine- and 5-Hydroxymethyl-uridine-Modified RNA", Synthesis, 2016, vol. 48, p. 1108-1116

SUMMARY OF INVENTION

Problem to be Solved by the Invention

As a result of studies for the synthesis of LNA, the inventors of the present invention have found that the amorphous form of the amidite of the bridged nucleoside has low stability. An object of the present invention is to solve the above problems of the amorphous form existing in the amidite form of the bridged nucleoside.

Methods for Solving the Problem

The inventors of the present invention have obtained crystals of an amidite form of a cytosine-type bridged nucleoside for the first time in the process of intensive research. Then, the present invention have found that the above crystals can solve the above problems of the amorphous form, and conducted further studies to complete the present invention. As used herein, the amidite form of the cytosine-type bridged nucleoside may be referred to as a "cytosine-type bridged nucleoside amidite", the crystal thereof may be referred to as a "cytosine-type bridged nucleoside amidite crystal", and the amidite form of the amorphous cytosine-type bridged nucleoside amidite may be abbreviated a "cytosine-type bridged nucleoside amidite amorphous".

Thus, the present invention relates to a cytosine-type bridged nucleoside amidite crystal represented by the following structural formula:

[Chem 1]

in which $R^1$ and $R^2$ each represents a substituent, and $R^3$ represents a protecting group.

The present invention also relates to a method for producing cytosine-type bridged nucleoside amidite crystals, comprising a step of dissolving a cytosine-type bridged nucleoside amidite amorphous in a nitrile solvent to obtain precipitated crystals.

Further, the present invention is a method for producing cytosine-type bridged nucleoside amidite crystals, comprising a step of dissolving a cytosine-type bridged nucleoside amidite amorphous in a readily soluble solvent and then adding an insoluble solvent.

Effects of Invention

According to the present invention, it is possible to provide cytosine-type bridged nucleoside amidite crystals and a method for producing the same, which have solved the above problems of the amorphous form existing in the amidite form of the bridged nucleoside. That is, the cytosine-type bridged nucleoside amidite crystals according to the present invention have improved stability and can be stably stored even under a high temperature condition of 50° C.

BRIEF DESCRIPTION OF DRAWINGS

FIG. 1 shows an appearance of crystal A of $N^4$-benzoyl-5'-O-(4,4'-dimethoxytrityl)-2'-O-4'-C-methylene-5-methyl-cytidine-3'-O—[O-(2-cyanoethyl)-N,N-diisopropylphos-phoramidite] obtained in Example 1.

FIG. 2 shows an appearance of crystal B of $N^4$-benzoyl-5'-O-(4,4'-dimethoxytrityl)-2'-O-4'-C-methylene-5-methyl-cytidine-3'-O—[O-(2-cyanoethyl)-N,N-diisopropylphos-phoramidite] obtained in Example 2.

FIG. 3 shows an appearance of crystal C of $N^4$-benzoyl-5'-O-(4,4'-dimethoxytrityl)-2'-O-4'-C-methylene-5-methyl-cytidine-3'-O—[O-(2-cyanoethyl)-N,N-diisopropylphos-phoramidite] obtained in Example 3.

FIG. 4 shows an X-ray diffraction spectrum of crystal A of $N^4$-benzoyl-5'-O-(4,4'-dimethoxytrityl)-2'-O-4'-C-methylene-5-methylcytidine-3'-O—[O-(2-cyanoethyl)-N,N-diisopropylphosphoramidite] obtained in Example 1; the vertical axis represents a diffraction intensity (CPS), and the horizontal axis represents a diffraction angle (2θ).

FIG. 5 shows an X-ray diffraction spectrum of crystal B of $N^4$-benzoyl-5'-O-(4,4'-dimethoxytrityl)-2'-O-4'-C-methylene-5-methylcytidine-3'-O—[O-(2-cyanoethyl)-N,N-diisopropylphosphoramidite] obtained in Example 2; the vertical axis represents a diffraction intensity (CPS), and the horizontal axis represents a diffraction angle (2θ).

FIG. 6 shows an X-ray diffraction spectrum of crystal C of $N^4$-benzoyl-5'-O-(4,4'-dimethoxytrityl)-2'-O-4'-C-methylene-5-methylcytidine-3'-O—[O-(2-cyanoethyl)-N,N-diisopropylphosphoramidite] obtained in Example 3; the vertical axis represents a diffraction intensity (CPS), and the horizontal axis represents a diffraction angle (2θ).

FIG. 7 shows a differential scanning calorimetry result of crystal A of $N^4$-benzoyl-5'-O-(4,4'-dimethoxytrityl)-2'-O-4'-C-methylene-5-methylcytidine-3'-O—[O-(2-cyanoethyl)-N,N-diisopropylphosphoramidite] obtained in Example 1, in which figure, the "DSC mW" on the vertical axis represents a change of calory, and the "Temp° C." on the horizontal axis represents a change of temperature.

FIG. 8 shows a differential scanning calorimetry result of crystal B of $N^4$-benzoyl-5'-O-(4,4'-dimethoxytrityl)-2'-O-4'-C-methylene-5-methylcytidine-3'-O—[O-(2-cyanoethyl)-N,N-diisopropylphosphoramidite] obtained in Example2, in which figure, the "DSC mW" on the vertical axis represents a change of calory, and the "Temp° C." on the horizontal axis represents a change of temperature.

FIG. 9 shows a differential scanning calorimetry result of crystal C of $N^4$-benzoyl-5'-O-(4,4'-dimethoxytrityl)-2'-O-4'-C-methylene-5-methylcytidine-3'-O—[O-(2-cyanoethyl)-N,N-diisopropylphosphoramidite] obtained in Example 3, in which figure, the "DSC mW" on the vertical axis represents a change of calory, and the "Temp° C." on the horizontal axis represents a change of temperature.

FIG. 10 shows a differential scanning calorimetry result of $N^4$-benzoyl-5'-O-(4,4'-dimethoxytrityl)-2'-O-4'-C-methylene-5-methylcytidine-3'-O—[O-(2-cyanoethyl)-N,N-diisopropylphosphoramidite] amorphous obtained in Comparative Example, in which figure, the "DSC mW" on the vertical axis represents a change of calory, and the "Temp° C." on the horizontal axis represents a change of temperature.

FIG. 11 shows stability test results of crystals A to C and a control amorphous form of $N^4$-benzoyl-5'-O-(4,4'-dimethoxytrityl)-2'-O-4'-C-methylene-5-methylcytidine-3'-O—[O-(2-cyanoethyl)-N,N-diisopropylphosphoramidite] obtained in Examples 1 to 3, in which figure, the vertical axis represents HPLC (%), and the horizontal axis represents the number of elapsed days.

DETAILED DESCRIPTION OF THE INVENTION

In one aspect, the present invention provides a cytosine-type bridged nucleoside amidite crystal represented by the following structural formula:

[Chem 2]

In the above formula, $R^1$ and $R^2$ each represents a substituent, and $R^3$ represents a protecting group. The substituent represented by $R^1$ is an acyl group such as an acetyl group, a propionyl group, an isobutyryl group and a benzoyl group; or an amino group protected by a dimethylaminomethylene group; or an amino group. The substituent represented by $R^2$ is a methyl group or a hydrogen atom. The protecting group represented by $R^3$ is a trityl group, a monomethoxytrityl group, a dimethoxytrityl group or a pixyl group. Among these, it is preferable that $R^1$ is a benzamido group, $R^2$ is a methyl group, and $R^3$ is a dimethoxytrityl group, from the viewpoint of general purpose.

The cytosine-type bridged nucleoside amidite crystals according to the present invention can take different crystal forms depending on the difference in conditions for obtaining crystals. For convenience, the crystalline polymorphs are referred to as crystal A, crystal B and crystal C as used herein.

The cytosine-type bridged nucleoside amidite crystals according to the present invention are obtained as columnar or dendrite crystals. A photograph of the appearance of the crystal A is shown in FIG. 1, a photograph of the appearance of the crystal B is shown in FIG. 2, and a photograph of the appearance of the crystal C is shown in FIG. 3.

When the cytosine-type bridged nucleoside amidite crystals according to the present invention are analyzed with a powder X-ray diffractometer using a Cu—Kα ray, the diffraction angle (2θ) has any one of the characteristic peak patterns of the crystal A, the crystal B and the crystal C, as shown below:

(Crystal A):
7.96, 8.94, 9.50, 10.49, 11.00, 11.12, 13.45, 13.82, 16.79, 17.76, 18.22, 19.14, 19.27, 19.84, 20.31, 20.60, 21.38, 22.65, 24.99, 25.33, and 26.42 (°);

(Crystal B):
8.09, 10.28, 10.59, 11.07, 11.38, 12.93, 13.50, 15.01, 16.73, 16.92, 17.43, 17.74, 18.77, 19.71, 20.51, 21.50, 21.74, 22.00, 22.22, 22.72, 23.43, 23.80, 24.13, 24.78, and 28.10(°);

(Crystal C):
8.06, 10.20, 10.52, 11.01, 11.35, 11.63, 12.92, 13.48, 14.93, 15.95, 16.68, 16.89, 17.33, 17.61, 18.50, 18.72, 19.70, 19.90, 20.49, 21.43, 21.85, 22.16, 22.57, 23.76, and 27.96 (°).

The peak pattern of the crystal A is shown in FIG. 4, the peak pattern of the crystal B is shown in FIG. 5, and the peak pattern of the crystal C is shown in FIG. 6.

In general, the diffraction angle (2θ) in powder X-ray diffraction may include an error range of less than 5%. The cytosine-type bridged nucleoside amidite crystals according to the present invention also include crystals having a completely matched diffraction angle in powder X-ray diffraction as well as crystals in which the diffraction angle is matched in an error of less than 5%. For example, the cytosine-type bridged nucleoside amidite crystals according to the present invention have any one of the characteristic peak patterns of the crystal A, the crystal B, and the crystal C shown below as the diffraction angles (2θ) in the powder X-ray diffraction:

(Crystal A):
7.96±0.40, 8.94±0.45, 9.50±0.48, 10.49±0.52, 11.00±0.55, 11.12±0.56, 13.45±0.67, 13.82±0.69, 16.79±0.84, 17.76±0.89, 18.22±0.91, 19.14±0.96, 19.27±0.96, 19.84±0.99, 20.31±1.02, 20.60±1.03, 21.38±1.07, 22.65±1.13, 24.99±1.25, 25.33±1.27, and 26.42±1.32 (°);

(Crystal B):
8.09±0.41, 10.28±0.51, 10.59±0.53, 11.07±0.55, 11.38±0.57, 12.93±0.65, 13.50±0.68, 15.01±0.75, 16.73±0.84, 16.92±0.85, 17.43±0.87, 17.74±0.89, 18.77±0.94, 19.71±0.99, 20.51±1.03, 21.50±1.08, 21.74±1.09, 22.00±1.10, 22.22±1.11, 22.72±1.14, 23.43±1.17, 23.80±1.19, 24.13±1.21, 24.78±1.24, and 28.10±1.41 (°);

(Crystal C):
8.06±0.40, 10.20±0.51, 10.52±0.53, 11.01±0.55, 11.35±0.57, 11.63±0.58, 12.92±0.65, 13.48±0.67, 14.93±0.75, 15.95±0.80, 16.68±0.83, 16.89±0.85, 17.33±0.87, 17.61±0.88, 18.50±0.93, 18.72±0.94, 19.70±0.99, 19.90±1.00, 20.49±1.02, 21.43±1.07, 21.85±1.09, 22.16±1.11, 22.57±1.13, 23.76±1.19, and 27.96±1.40 (°).

It should be noted that, in this specification, the powder X-ray diffraction is performed under the following conditions:

Device used: X-ray diffractometer X'Pert PRO MPD (Spectris);
Target: Cu;
X-ray tube current: 40 mA;
X-ray tube voltage: 45 kV; and
Scanning range: 2θ=4.0 to 40.0°.

When the cytosine-type bridged nucleoside amidite crystals according to the present invention are analyzed with a differential scanning calorimeter (manufactured by Shimadzu Corporation) (at a heating rate of 5° C./min), the endothermic peaks due to melting are shown around 96, 176, and 184° C. (an error of ±2° C.) for the crystal A, as shown in FIG. 8; and around 148, and 183° C. (an error of ±2° C.) for the crystal B, as shown in FIG. 8; and around 177 and 183° C. (an error of ±2° C.) for the crystal C, as shown in FIG. 9. On the other hand, the amorphous did not show any endothermic peak as shown in FIG. 10.

The cytosine-type bridged nucleoside amidite crystals according to the present invention have extremely high stability, and have a suppressed decomposition degree of less than or equal to 1%, even if they are stored at 50° C. for 20 days, for example, as demonstrated in Examples described below.

As used herein, the term "decomposition degree" is defined as a value obtained by subtracting a purity of a cytosine-type bridged nucleoside amidite crystal after storage from a purity of the crystal at the start of a stability test when the stability test is performed for a certain period of time under the following conditions. The purity can be determined by HPLC. A higher decomposition degree means that the decomposition progressed and the purity decreased.

(Stability Test Conditions)

Temperature: 50° C.;

Storage conditions: 20 mg of crystal is placed in a glass vial and stored in a tightly sealed state;

(HPLC Conditions)

Column: YMC-Triart C18, 150×4.6 mm I.D. (manufactured by YMC);

Eluent: 5 mM triethylammonium acetate (pH 7.0) containing 80 vol % acetonitrile; and Detection method: detection by UV 280 nm.

In another aspect, the present invention provides a method for producing the cytosine-type bridged nucleoside amidite crystals.

The cytosine-type bridged nucleoside amidite crystals according to the present invention can be obtained by utilizing the low affinity of the phosphoramidite group to the nitrile solvent. That is, the cytosine-type bridged nucleoside amidite crystals according to the present invention can be obtained by dissolving the cytosine-type bridged nucleoside amidite amorphous in a nitrile solvent to precipitate crystals (Method A). Alternatively, as another method, the cytosine-type bridged nucleoside amidite crystals can be obtained by dissolving the cytosine-type bridged nucleoside amidite amorphous in a readily soluble solvent and then adding an insoluble solvent (Method B).

A specific example of the method A includes a method of performing an addition reaction of the phosphoramidite group as shown in the following chemical formula 3 and a common purification operation, and then dissolving the resulting cytosine-type bridged nucleoside amidite amorphous in a nitrile solvent once, and then precipitating crystals. In this case, operations such as stirring and cooling are not particularly necessary, but these operations may be performed.

[Chem 3]

In the above formula, $R^1$ and $R^2$ each represents the substituent, and $R^3$ represents the protecting group.

In this case, the nitrile solvent that can be used herein includes acetonitrile, propionitrile, butyronitrile, valeronitrile, benzonitrile, and the like. Among them, acetonitrile and propionitrile are preferred in terms of safety and handling, and acetonitrile is more preferred in terms of cost. On the other hand, in the method A, it is important not to contain a protic polar solvent such as methanol and ethanol, and a non-polar solvent such as dichloromethane, ethyl acetate, chloroform and tetrahydrofuran, because these solvents have higher solubility of the compound.

A specific example of the method B includes a method of dissolving a cytosine-type bridged nucleoside amidite amorphous obtained in the same manner as the method A once in a readily soluble solvent, and then adding an insoluble solvent to precipitate crystals. Examples of the readily soluble solvent include alcohol solvents such as methanol, ethanol, isopropanol, tert-butanol and n-butanol; ketone solvents such as acetone and butanone; halogen solvents such as dichloromethane and chloroform; ester solvents such as ethyl acetate and butyl acetate; and ether solvents such as tetrahydrofuran and tert-butyl methyl ether. Examples of the insoluble solvent that can be used herein include hydrocarbon solvents such as pentane, hexane, and heptane.

The step of obtaining the crystals as described above may add operations such as cooling of the solution, addition of seed crystals, and ultrasonic irradiation in order to obtain crystals more efficiently.

A person skilled in the art will also be able to carry out the synthesis step by appropriately referring to known literature (Tetrahedron 1998, 54, 3607-3630, or the like). Examples of the synthesis step may include a step of causing a combination of 2-cyanoethyl-N,N,N',N'-tetraisopropylphosphoramidite and tetrazole or substituted tetrazole or a combination of 2-cyanoethyl-N,N-diisopropylchlorophosphoramidite and diisopropylethylamine to react in an organic solvent such as acetonitrile or dichloromethane at room temperature for 2 to 3 hours, confirming disappearance of the starting materials by thin layer chromatography (TLC) or HPLC, and then performing normal post-treatment.

The cytosine-type bridged nucleoside amidite thus synthesized can be purified by chromatography using silica gel or the like as a carrier, and then dissolved in the nitrile solvent, and further subjected to operations such as addition of the insoluble solvent, addition of seed crystals, cooling, and stirring, thereby precipitating it as crystals.

The cytosine-type bridged nucleoside amidite crystals obtained by the production method as described above can be filtered by a filtration method such as pressure filtration, vacuum filtration, basket separation, and filter press, and then dried to obtain a product. The drying may employ a method such as conical drying, vacuum drying including shelf drying, fluidized bed drying, ventilation drying including shelf drying, and spray drying as needed.

EXAMPLES

Hereinafter, the present invention will be specifically described with reference to Examples, but it would be clear that the present invention is not limited to these Examples.

(Example 1: Crystal A) Preparation of
5-Methylcytosine-Type Bridged Nucleoside Amidite
($R^1$=a Benzamido Group, $R^2$=a Methyl Group,
$R^3$=a Dimethoxytrityl Group) Crystal A 5-methylcytosine-type bridged nucleoside amidite ($R^1$=a benzamido group, $R^2$=a methyl group, $R^3$=a dimethoxytrityl group) was prepared according to the method described in the known literature (Tetrahedron 1998, 54, 3607-3630).

0.65 g of the resulting amorphous 5-methylcytosine-type bridged nucleoside amidite ($R^1$=a benzamido group, $R^2$=a methyl group, $R^3$=a dimethoxytrityl group) was dissolved in 5 mL of acetonitrile and allowed to stand at −20° C. for 7 days to precipitate crystals.

The resulting crystals were collected by suction filtration and dried in a vacuum to obtain the 5-methylcytosine-type bridged nucleoside amidite ($R^1$=a benzamido group, $R^2$=a methyl group, $R^3$=a dimethoxytrityl group) crystal (0.35 g).

(Example 2: Crystal B) Preparation of
5-Methylcytosine-Type Bridged Nucleoside Amidite
($R^1$=a Benzamido Group, $R^2$=a Methyl Group,
$R^3$=a Dimethoxytrityl Group) Crystal A 5-methylcytosine-type bridged nucleoside amidite ($R^1$=a benzamido group, $R^2$=a methyl group, $R^3$=a dimethoxytrityl group) was prepared according to the method described in the known literature (Tetrahedron 1998, 54, 3607-3630).

After dissolving 1.00 g of the resulting amorphous 5-methylcytosine-type bridged nucleoside amidite ($R^1$=a benzamido group, $R^2$=a methyl group, $R^3$=a dimethoxytrityl group) in 1 mL of dichloromethane, 15 mL of hexane was gradually added. This solution was irradiated with ultrasonic waves to precipitate crystals. To the solution was further added 10 mL of hexane, and allowed to stand for 3 hours. The crystals precipitated in the solution were collected by suction filtration and dried in a vacuum to obtain the 5-methylcytosine-type bridged nucleoside amidite ($R^1$=a benzamido group, $R^2$=a methyl group, $R^3$=a dimethoxytrityl group) crystal (0.81 g).

(Example 3: Crystal C) Preparation of
5-Methylcytosine-Type Bridged Nucleoside Amidite
($R^1$=a Benzamido Group, $R^2$=a Methyl Group,
$R^3$=a Dimethoxytrityl Group) Crystal A 5-methylcytosine-type bridged nucleoside amidite ($R^1$=a benzamido group, $R^2$=a methyl group, $R^3$=a dimethoxytrityl group) was prepared according to the method described in the known literature (Tetrahedron 1998, 54, 3607-3630).

1.00 g of the resulting amorphous 5-methylcytosine-type bridged nucleoside amidite ($R^1$=a benzamido group, $R^2$=a methyl group, $R^3$=a dimethoxytrityl group) was dissolved in 1 mL of acetonitrile and allowed to stand at –20° C. for 2 hours to precipitate crystals (0.80 g).

(Comparative Example) Case where Only Dichloromethane or Dichloromethane-acetonitrile (1:1) was Used as a Crystallization Solvent An amorphous 5-methylcytosine-type bridged nucleoside amidite was obtained by the method described in Example 1. The crystallization was examined under the same conditions as those of Example 1, with the exception that the dissolving solvent was changed from acetonitrile to only dichloromethane or dichloromethane-acetonitrile (1:1). However, no crystal was precipitated.

(Example 4) Analysis of Various Physical Properties of Crystals

Various physical properties of the 5-methylcytosine-type bridged nucleoside amidite ($R^1$=a benzamido group, $R^2$=a methyl group, $R^3$=a dimethoxytrityl group) crystals obtained in Examples 1, 2, and 3 were analyzed.

(a) Crystal Form

FIG. 1 shows a photograph of the appearance of the crystal A of 5-methylcytosine-type bridged nucleoside amidite ($R^1$=a benzamido group, $R^2$=a methyl group, $R^3$=a dimethoxytrityl group) obtained in Example 1. As shown in FIG. 1, it was found that the 5-methylcytosine-type bridged nucleoside amidite crystal had a columnar crystal form.

Each of 5-methylcytosine-type bridged nucleoside amidites obtained in Examples 2 and 3 also showed the appearance of the columnar or dendritic crystal, although the crystal sizes were different. FIG. 2 shows a photograph of the appearance of the crystal B obtained in Example 2, and FIG. 3 shows a photograph of the appearance of the crystal C obtained in Example 3.

(b) Measurement of Purity

The purity of the 5-methylcytosine-type bridged nucleoside amidite ($R^1$=a benzamido group, $R^2$=a methyl group, $R^3$=a dimethoxytrityl group) crystal A obtained in Example 1 above was analyzed by HPLC. As a result, the purity of the 5-methylcytosine-type bridged nucleoside amidite crystal A was 98.8%. The HPLC method was performed under the following conditions:

(HPLC Conditions)

Column: YMC-Triart C18, 150×4.6 mm I.D. (manufactured by YMC);
Eluent: 5 mM triethylammonium acetate (pH 7.0) containing 80 vol % acetonitrile; and
Detection method: detection by UV 280 nm.

The purities of the 5-methylcytosine-type bridged nucleoside amidite crystals B and C obtained in Examples 2 and 3 above were also measured under the same conditions. The purity of 5-methylcytosine-type bridged nucleoside amidite crystal B was 98.7%, and the purity of the 5-methylcytosine type bridged nucleoside amidite crystal C obtained in Example 3 was 98.6%.

(c) Powder X-Ray Diffraction

X-ray diffraction spectra of the 5-methylcytosine-type bridged nucleoside amidite ($R^1$=a benzamido group, $R^2$=a methyl group, $R^3$=a dimethoxytrityl group) crystals A, B and C obtained in Examples 1 to 3 were analyzed using an X-ray diffractometer X'Pert PRO MPD (Spectris) under the following measurement conditions:

(Measurement Conditions)

Target: Cu;
X-ray tube current: 40 mA;
X-ray tube voltage: 45 kV; and
Scanning range: $2\theta$=4.0 to 40.0°.

As shown in FIG. 4 and Table 1, the 5-methylcytosine-type bridged nucleoside amidite ($R^1$=a benzamido group, $R^2$=a methyl group, $R^3$=a dimethoxytrityl group) crystal A had a diffraction angle ($2\theta$) showing peaks around:

(Crystal A):

7.96, 8.94, 9.50, 10.49, 11.00, 11.12, 13.45, 13.82, 16.79, 17.76, 18.22, 19.14, 19.27, 19.84, 20.31, 20.60, 21.38, 22.65, 24.99, 25.33, and 26.42 (°), in particular, showing characteristic peaks around 7.96, 11.00, 13.45, 13.82, 16.79, 17.76, and 20.60 (°).

TABLE 1

| No. | Pos. [°2Th] | d value [A] | NET Intensity [cts] | Relative Intensity [%] |
|---|---|---|---|---|
| 1 | 7.96 | 11.10 | 6652 | 100.00 |
| 2 | 8.94 | 9.89 | 1249 | 18.78 |
| 3 | 9.50 | 9.31 | 2033 | 30.57 |
| 4 | 10.49 | 8.43 | 1660 | 24.97 |
| 5 | 11.00 | 8.04 | 2710 | 40.74 |
| 6 | 11.12 | 7.96 | 1668 | 25.08 |
| 7 | 12.39 | 7.15 | 105 | 1.58 |
| 8 | 13.05 | 6.78 | 588 | 8.84 |
| 9 | 13.45 | 6.58 | 2700 | 40.60 |
| 10 | 13.82 | 6.41 | 3653 | 54.91 |
| 11 | 14.45 | 6.13 | 383 | 5.76 |
| 12 | 14.96 | 5.92 | 221 | 3.32 |
| 13 | 15.99 | 5.54 | 181 | 2.71 |
| 14 | 16.44 | 5.39 | 687 | 10.33 |
| 15 | 16.79 | 5.28 | 4795 | 72.08 |
| 16 | 17.20 | 5.16 | 562 | 8.45 |
| 17 | 17.76 | 5.00 | 3255 | 48.93 |
| 18 | 18.22 | 4.87 | 1037 | 15.59 |
| 19 | 18.66 | 4.75 | 657 | 9.88 |
| 20 | 19.14 | 4.64 | 1427 | 21.45 |
| 21 | 19.27 | 4.61 | 1083 | 16.28 |
| 22 | 19.84 | 4.48 | 1207 | 18.15 |
| 23 | 20.31 | 4.37 | 1717 | 25.82 |
| 24 | 20.60 | 4.31 | 4203 | 63.19 |
| 25 | 21.06 | 4.22 | 907 | 13.63 |
| 26 | 21.38 | 4.16 | 2232 | 33.55 |
| 27 | 21.87 | 4.06 | 514 | 7.73 |
| 28 | 22.13 | 4.02 | 347 | 5.22 |
| 29 | 22.65 | 3.93 | 1177 | 17.69 |
| 30 | 23.33 | 3.81 | 891 | 13.40 |
| 31 | 23.91 | 3.72 | 571 | 13.09 |
| 32 | 24.32 | 3.66 | 906 | 13.62 |
| 33 | 24.64 | 3.61 | 367 | 5.52 |
| 34 | 24.99 | 3.56 | 1061 | 15.95 |
| 35 | 25.33 | 3.52 | 1569 | 23.59 |
| 36 | 25.99 | 3.43 | 286 | 4.29 |
| 37 | 26.42 | 3.37 | 1201 | 18.05 |
| 38 | 26.98 | 3.30 | 390 | 5.86 |
| 39 | 28.13 | 3.17 | 480 | 7.21 |
| 40 | 28.72 | 3.11 | 247 | 3.72 |
| 41 | 29.53 | 3.03 | 692 | 10.40 |
| 42 | 30.30 | 2.95 | 128 | 1.93 |
| 43 | 31.82 | 2.81 | 195 | 2.93 |
| 44 | 33.30 | 2.69 | 156 | 2.34 |
| 45 | 34.12 | 2.63 | 154 | 2.32 |
| 46 | 35.82 | 2.51 | 206 | 3.09 |
| 47 | 36.43 | 2.47 | 162 | 2.44 |
| 48 | 37.30 | 2.41 | 154 | 2.31 |
| 49 | 38.25 | 2.35 | 146 | 2.19 |
| 50 | 39.01 | 2.31 | 86 | 1.30 |

As shown in FIG. 5 and Table 2, the 5-methylcytosine-type bridged nucleoside amidite ($R^1$=a benzamido group, $R^2$=a methyl group, $R^3$=a dimethoxytrityl group) crystal B obtained in Example 2 had a diffraction angle (2θ) showing characteristic peaks around:

(Crystal B):

8.09, 10.28, 10.59, 11.07, 11.38, 12.93, 13.50, 15.01, 16.73, 16.92, 17.43, 17.74, 18.77, 19.71, 20.51, 21.50, 21.74, 22.00, 22.22, 22.72, 23.43, 23.80, 24.13, 24.78, and 28.10 (°).

TABLE 2

| No. | Pos. [°2Th] | d value [A] | NET Intensity [cts] | Relative Intensity [%] |
|---|---|---|---|---|
| 1 | 5.80 | 15.20 | 102 | 1.93 |
| 2 | 8.09 | 10.90 | 4421 | 84.19 |
| 3 | 10.28 | 8.60 | 1208 | 23.00 |
| 4 | 10.59 | 8.36 | 1263 | 24.05 |
| 5 | 11.07 | 8.00 | 5082 | 96.78 |
| 6 | 11.38 | 7.78 | 1192 | 22.70 |
| 7 | 11.72 | 7.55 | 599 | 11.40 |
| 8 | 12.40 | 7.14 | 139 | 2.64 |
| 9 | 12.93 | 6.85 | 1613 | 30.71 |
| 10 | 13.50 | 6.56 | 5251 | 100.00 |
| 11 | 13.84 | 6.40 | 537 | 10.22 |
| 12 | 14.38 | 6.16 | 706 | 13.45 |
| 13 | 15.01 | 5.90 | 1170 | 22.28 |
| 14 | 16.03 | 5.53 | 722 | 13.75 |
| 15 | 16.21 | 5.47 | 549 | 10.45 |
| 16 | 16.73 | 5.30 | 2063 | 39.28 |
| 17 | 16.92 | 5.24 | 1775 | 33.81 |
| 18 | 17.43 | 5.09 | 4516 | 86.00 |
| 19 | 17.74 | 5.00 | 2298 | 43.75 |
| 20 | 18.77 | 4.73 | 4627 | 88.11 |
| 21 | 19.71 | 4.50 | 2259 | 43.03 |
| 22 | 20.51 | 4.33 | 1986 | 37.83 |
| 23 | 21.17 | 4.20 | 681 | 12.98 |
| 24 | 21.50 | 4.13 | 1992 | 39.93 |
| 25 | 21.74 | 4.09 | 2174 | 41.40 |
| 26 | 22.00 | 4.04 | 1401 | 26.69 |
| 27 | 22.22 | 4.00 | 1520 | 28.95 |
| 28 | 22.72 | 3.91 | 2078 | 39.57 |
| 29 | 23.43 | 3.80 | 991 | 18.88 |
| 30 | 23.80 | 3.74 | 1200 | 22.85 |
| 31 | 24.13 | 3.69 | 952 | 18.13 |
| 32 | 24.78 | 3.59 | 1044 | 19.88 |
| 33 | 25.17 | 3.54 | 651 | 12.40 |
| 34 | 25.88 | 3.44 | 399 | 7.59 |
| 35 | 26.54 | 3.36 | 309 | 5.89 |
| 36 | 27.32 | 3.27 | 321 | 6.12 |
| 37 | 27.74 | 3.22 | 340 | 6.48 |
| 38 | 28.10 | 3.18 | 933 | 17.77 |
| 39 | 28.94 | 3.09 | 465 | 8.86 |
| 40 | 29.44 | 3.03 | 345 | 6.56 |
| 41 | 30.21 | 2.96 | 323 | 6.16 |
| 42 | 31.31 | 2.86 | 243 | 4.62 |
| 43 | 31.88 | 2.81 | 217 | 4.14 |
| 44 | 32.72 | 2.74 | 197 | 3.75 |
| 45 | 33.77 | 2.65 | 176 | 3.34 |
| 46 | 35.75 | 2.51 | 170 | 3.24 |
| 47 | 38.28 | 2.35 | 105 | 2.00 |

As shown in FIG. 6 and Table 3, the 5-methylcytosine-type bridged nucleoside amidite ($R^1$=a benzamido group, $R^2$=a methyl group, $R^3$=a dimethoxytrityl group) crystal C obtained in Example 3 had a diffraction angle (2θ) showing characteristic peaks around:

(Crystal C):

8.06, 10.20, 10.52, 11.01, 11.35, 11.63, 12.92, 13.48, 14.93, 15.95, 16.68, 16.89, 17.33, 17.61, 18.50, 18.72, 19.70, 19.90, 20.49, 21.43, 21.85, 22.16, 22.57, 23.76, and 27.96 (°).

TABLE 3

| No. | Pos. [°2Th] | d value [A] | NET Intensity [cts] | Relative Intensity [%] |
|---|---|---|---|---|
| 1 | 5.75 | 15.40 | 194 | 2.05 |
| 2 | 8.06 | 11.00 | 6831 | 71.94 |
| 3 | 9.67 | 9.15 | 990 | 10.42 |
| 4 | 10.20 | 8.68 | 6459 | 68.02 |
| 5 | 10.52 | 8.41 | 1460 | 15.38 |
| 6 | 11.01 | 8.39 | 5626 | 59.25 |
| 7 | 11.35 | 7.79 | 1425 | 15.01 |
| 8 | 11.63 | 7.61 | 2326 | 24.49 |
| 9 | 12.92 | 6.85 | 1979 | 20.84 |
| 10 | 13.48 | 6.57 | 6587 | 69.37 |
| 11 | 13.86 | 6.39 | 698 | 7.35 |
| 12 | 14.34 | 6.18 | 857 | 9.02 |
| 13 | 14.93 | 5.93 | 3446 | 36.29 |
| 14 | 15.95 | 5.56 | 1537 | 16.18 |
| 15 | 16.19 | 5.47 | 845 | 8.89 |
| 16 | 16.68 | 5.32 | 2386 | 25.13 |
| 17 | 16.89 | 5.25 | 2450 | 25.80 |
| 18 | 17.33 | 5.12 | 9495 | 100.00 |
| 19 | 17.61 | 5.04 | 7013 | 73.86 |
| 20 | 18.50 | 4.80 | 7672 | 80.80 |
| 21 | 18.72 | 4.74 | 6121 | 64.46 |
| 22 | 19.70 | 4.51 | 3240 | 34.12 |
| 23 | 19.90 | 4.46 | 1569 | 16.53 |
| 24 | 20.49 | 4.34 | 2370 | 24.96 |
| 25 | 21.14 | 4.20 | 894 | 9.42 |
| 26 | 21.43 | 4.15 | 1865 | 19.64 |
| 27 | 21.85 | 4.07 | 5346 | 56.31 |
| 28 | 22.16 | 4.01 | 1554 | 16.36 |
| 29 | 22.57 | 3.94 | 5578 | 58.74 |
| 30 | 23.34 | 3.81 | 1346 | 14.17 |
| 31 | 23.76 | 3.74 | 1793 | 18.88 |
| 32 | 24.06 | 3.70 | 1027 | 10.81 |
| 33 | 24.70 | 3.60 | 1155 | 12.16 |
| 34 | 25.12 | 3.55 | 800 | 8.42 |
| 35 | 25.79 | 3.45 | 460 | 4.84 |
| 36 | 26.41 | 3.38 | 749 | 7.89 |
| 37 | 27.21 | 3.28 | 401 | 4.22 |
| 38 | 27.65 | 3.23 | 739 | 7.78 |
| 39 | 27.96 | 3.19 | 1761 | 18.55 |
| 40 | 28.92 | 3.09 | 523 | 5.50 |
| 41 | 29.34 | 3.04 | 883 | 9.30 |
| 42 | 30.04 | 2.98 | 519 | 5.47 |
| 43 | 31.04 | 2.88 | 335 | 3.53 |
| 44 | 31.76 | 2.82 | 337 | 3.55 |
| 45 | 32.75 | 2.73 | 241 | 2.54 |
| 46 | 33.20 | 2.70 | 173 | 1.82 |
| 47 | 33.64 | 2.66 | 256 | 2.70 |
| 48 | 35.08 | 2.56 | 3.66 | 3.86 |
| 49 | 35.71 | 2.51 | 328 | 3.45 |
| 50 | 36.78 | 2.44 | 160 | 1.68 |
| 51 | 38.18 | 2.36 | 324 | 3.42 |
| 52 | 38.74 | 2.33 | 143 | 1.50 |

(d) Differential Scanning Calorimetry

The 5-methylcytosine-type bridged nucleoside amidite ($R^1$=a benzamido group, $R^2$=a methyl group, $R^3$=a dimethoxytrityl group) crystals A to C were analyzed with a differential scanning calorimetry (DSC) device (at a heating rate of 5° C./min). The crystal A showed endothermic peaks due to melting around 96, 176, and 184° C. (an error ±2° C.) as shown in FIG. 7, the crystal B showed endothermic peaks due to melting around 148 and 183° C. (an error ±2° C.) as shown in FIG. 8, the crystal C showed the endothermic peaks due to melting around 177 and 183° C. (an error ±2° C.) as shown in FIG. 9. On the other hand, the amorphous did not have any endothermic peak as shown in FIG. 10.

(Example 5) Stability Comparison of 5-Methylcytosine-Type Bridged Nucleoside Amidite Crystal to Known Amorphous Form The stability of each of 5-methylcytosine-type bridged nucleoside amidite ($R^1$=a benzamido group, $R^2$=a methyl group, $R^3$=a dimethoxytrityl group) crystals A to C obtained in Examples 1, 2, and 3, to the stability of the amorphous form obtained in Comparative Example were compared by the method described below.

(Stability Test Conditions)

Temperature: 50° C.;

Storage conditions: 20 mg of each of crystals A to C or amorphous form was placed in a glass vial and stored in a tightly sealed state; and Sampling time: after 1, 2, 3, 4, 6, and 20 (days), each specimen was sampled and subjected to HPLC analysis;

(HPLC Conditions)

Column: YMC-Triart C18, 150×4.6 mm I.D. (manufactured by YMC)

Eluent: 5 mM triethylammonium acetate (pH 7.0) containing 80 vol % acetonitrile; and Detection method: detection by UV 280 nm.

The results of the stability test are shown in FIG. 11 and Table 4. The leftmost column in the table indicates the number of elapsed days, and the column "Example 1 (Crystal A)" indicates the HPLC purity of the crystal A of the 5-methylcytosine-type bridged nucleoside amidite obtained in Example 1 ($R^1$=a benzamido group, $R^2$=a methyl group, $R^3$=a dimethoxytrityl group) after the corresponding number of elapsed days, and the column "Example 2 (crystal B)" indicates the HPLC purity of the crystal B of the 5-methylcytosine-type bridged nucleoside amidite obtained in Example 2 ($R^1$=a benzamido group, $R^2$=a methyl group, $R^3$=a dimethoxytrityl group) after the corresponding number of elapsed days, and the column "Example 3 (Crystal C) indicates the HPLC purity of the crystal C of 5-methylcytosine-type bridged nucleoside amidite obtained in Example 3 ($R^1$=a benzamido group, $R^2$=a methyl group, $R^3$=a dimethoxytrityl group) after the corresponding number of elapsed days, and the column "Control" indicates the HPLC purity of the amorphous form used as a control after the corresponding number of elapsed days. In the table, the cells marked by "-" indicate that no measurement was performed. The "Decomposition Degree (Δ%)" at the bottom shows the difference when the HPLC purity after 20 days is subtracted from the HPLC purity on day 0, which means that the larger this value, the more decomposition occurred.

TABLE 4

| Days | HPLC (%) | | | |
| | Example 1 (Crystal A) | Example 2 (Crystal 8 ) | Example 3 (Crystal C) | Control (Amorphous) |
| --- | --- | --- | --- | --- |
| 0 | 98.8 | 98.7 | 98.6 | 98.7 |
| 1 | 98.4 | 98.7 | 98.7 | 98.2 |
| 2 | 98.1 | 98.6 | 98.6 | 97.9 |
| 3 | 98.3 | — | — | 97.9 |
| 4 | — | 98.6 | 98.5 | — |
| 6 | 98.1 | 98.5 | 98.5 | 96.9 |
| 20 | 98.1 | 98.3 | 98.1 | 92.1 |
| Decomposition Degree(Δ %) | 0.7 | 0.4 | 0.5 | 6.6 |

It was found from the above results that even if the 5-methylcytosine-type bridged nucleoside amidite ($R^1$=a benzamido group, $R^2$=a methyl group, $R^3$=a dimethoxytrityl group) crystals A to C obtained in Examples 1 to 3 were stored under a condition of 50° C. for 20 days, no decomposition of 1% or more in HPLC purity was observed, indicating extremely high stability. Further, it was understood that the amorphous form as a control had a decomposition degree of 6.6%, indicating that the 5-methylcytosine-type bridged nucleoside amidite crystals according to the present invention had significantly high stability as compared to that of the existing 5-methylcytosine-type bridged nucleoside amidite product.

The invention claimed is:

1. A cytosine-type bridged nucleoside amidite crystal represented by the following structural formula:

in which $R^1$ is a benzamido group, $R^2$ is a methyl group, and $R^3$ is a dimethoxytrityl group, and the cytosine-type bridged nucleoside amidite crystal has any one of characteristic peak patterns of crystal A, crystal B, and crystal C shown below, as a diffraction angle (2θ) of powder X-ray diffraction using a Cu-Kα ray:

(Crystal A):
7.96±0.40, 8.94±0.45, 9.50±0.48, 10.49±0.52, 11.00±0.55, 11.12±0.56, 13.45±0.67, 13.82±0.69, 16.79±0.84, 17.76±0.89, 18.22±0.91, 19.14±0.96, 19.27±0.96, 19.84±0.99, 20.31±1.02, 20.60±1.03, 21.38±1.07, 22.65±1.13, 24.99±1.25, 25.33±1.27, 26.42±1.32 (°);

(Crystal B):
8.09±0.41, 10.28±0.51, 10.59±0.53, 11.07±0.55, 11.38±0.57, 12.93±0.65, 13.50±0.68, 15.01±0.75, 16.73±0.84, 16.92±0.85, 17.43±0.87, 17.74±0.89, 18.77±0.94, 19.71±0.99, 20.51±1.03, 21.50±1.08, 21.74±1.09, 22.00±1.10, 22.22±1.11, 22.72±1.14, 23.43±1.17, 23.80±1.19, 24.13±1.21, 24.78±1.24, 28.10±1.41 (°); and (Crystal C):
8.06±0.40, 10.20±0.51, 10.52±0.53, 11.01±0.55, 11.35±0.57, 11.63±0.58, 12.92±0.65, 13.48±0.67, 14.93±0.75, 15.95±0.80, 16.68±0.83, 16.89±0.85, 17.33±0.87, 17.61±0.88, 18.50±0.93, 18.72±0.94, 19.70±0.99, 19.90±1.00, 20.49±1.02, 21.43±1.07, 21.85±1.09, 22.16±1.11, 22.57±1.13, 23.76±1.19, 27.96±1.40 (°).

2. A method for producing the cytosine-type bridged nucleoside amidite crystals according to claim 1, comprising a step of dissolving a cytosine-type bridged nucleoside amidite amorphous in a nitrile solvent to obtain precipitated crystals.

3. A method for producing the cytosine-type bridged nucleoside amidite crystals according to claim 1, comprising a step of dissolving a cytosine-type bridged nucleoside amidite amorphous in a readily soluble solvent and then adding an insoluble solvent.

4. The method for producing the cytosine-type bridged nucleoside amidite crystals according to claim 3, wherein the readily soluble solvent is one or more solvents selected from alcohol solvents, ketone solvents, halogen solvents, ester solvents, and ether solvents, and the insoluble solvent is a hydrocarbon solvent.

\* \* \* \* \*